United States Patent
Mansker et al.

(10) Patent No.: US 10,993,618 B2
(45) Date of Patent: *May 4, 2021

(54) DEPENDENCY-BASED STARTUP IN A MULTI-MODALITY MEDICAL SYSTEM

(71) Applicant: VOLCANO CORPORATION, San Diego, CA (US)

(72) Inventors: Richard E. Mansker, Sacramento, CA (US); Michael A. Echeverria, Elk Grove, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 35 days.

This patent is subject to a terminal disclaimer.

(21) Appl. No.: 16/455,245

(22) Filed: Jun. 27, 2019

(65) Prior Publication Data
US 2019/0313909 A1    Oct. 17, 2019

Related U.S. Application Data

(63) Continuation of application No. 14/067,713, filed on Oct. 30, 2013, now Pat. No. 10,335,034.
(Continued)

(51) Int. Cl.
*G06F 15/177* (2006.01)
*G06F 9/00* (2006.01)
(Continued)

(52) U.S. Cl.
CPC .......... *A61B 5/0035* (2013.01); *A61B 5/0036* (2018.08); *A61B 6/4417* (2013.01);
(Continued)

(58) Field of Classification Search
None
See application file for complete search history.

(56) References Cited

U.S. PATENT DOCUMENTS 7,389,410 B1    6/2008  Hardman
10,335,034 B2 *  7/2019  Mansker ............... G16H 10/60
(Continued)

FOREIGN PATENT DOCUMENTS

KR    1020090000839 A    1/2009

OTHER PUBLICATIONS

International Search Report and Written Opinion received in PCT Application No. PCT/US2013/067565, dated Feb. 27, 2014, 10 pages.

*Primary Examiner* — Tanh Q Nguyen

(57) ABSTRACT

A dependency-based startup method in a multi-modality medical processing system that includes receiving initialization information about a plurality of executable components to be started, the plurality of executable components including an executable modality component configured to communicate with a medical device communicatively coupled to the multi-modality medical processing system. The method also includes receiving dependency information about the executable modality component, the dependency information identifying one or more of the executable components upon which the executable modality component depends and transforming the initialization information and the dependency information into a dependency map that represents the dependencies between the plurality of executable components. Further, the method includes deriving a start order for the plurality of executable components based on the dependency map and starting the plurality of executable components in the multi-modality medical processing system according to the start order.

20 Claims, 5 Drawing Sheets

Related U.S. Application Data

(60) Provisional application No. 61/720,816, filed on Oct. 31, 2012.

(51) Int. Cl.

| | | |
|---|---|---|
| *G06F 9/24* | (2006.01) | |
| *A61B 8/14* | (2006.01) | |
| *A61B 6/00* | (2006.01) | |
| *A61B 5/05* | (2021.01) | |
| *A61B 5/00* | (2006.01) | |
| *A61B 8/12* | (2006.01) | |
| *A61B 8/00* | (2006.01) | |
| *G16H 10/60* | (2018.01) | |
| *G16H 40/63* | (2018.01) | |
| *G16H 40/40* | (2018.01) | |
| *A61B 18/02* | (2006.01) | |
| *A61B 5/026* | (2006.01) | |
| *A61B 5/029* | (2006.01) | |
| *A61B 5/055* | (2006.01) | |
| *A61B 18/14* | (2006.01) | |
| *A61B 18/00* | (2006.01) | |
| *A61B 90/00* | (2016.01) | |

(52) U.S. Cl.
CPC .............. *A61B 6/481* (2013.01); *A61B 8/12* (2013.01); *A61B 8/4416* (2013.01); *G16H 10/60* (2018.01); *G16H 40/40* (2018.01); *G16H 40/63* (2018.01); *A61B 5/0066* (2013.01); *A61B 5/0095* (2013.01); *A61B 5/029* (2013.01); *A61B 5/0261* (2013.01); *A61B 5/055* (2013.01); *A61B 5/4836* (2013.01); *A61B 8/54* (2013.01); *A61B 18/02* (2013.01); *A61B 18/1492* (2013.01); *A61B 2018/00791* (2013.01); *A61B 2090/378* (2016.02); *A61B 2560/029* (2013.01)

(56) References Cited

U.S. PATENT DOCUMENTS

| | | | |
|---|---|---|---|
| 10,799,209 B2 * | 10/2020 | Lahti | G16H 30/40 |
| 10,847,264 B2 * | 11/2020 | Mansker | G16H 40/00 |
| 10,869,603 B2 * | 12/2020 | Millett | A61B 5/02007 |
| 2002/0147903 A1 | 10/2002 | Hubert et al. | |
| 2007/0036402 A1 | 2/2007 | Cahill | |
| 2007/0173717 A1 | 7/2007 | Camus | |
| 2009/0292181 A1 | 11/2009 | Donaldson | |
| 2010/0318780 A1 | 12/2010 | Arditti et al. | |
| 2011/0077523 A1 | 3/2011 | Angott | |
| 2019/0313909 A1 * | 10/2019 | Mansker | A61B 6/4417 |

* cited by examiner

DEPENDENCY-BASED STARTUP IN A MULTI-MODALITY MEDICAL SYSTEM

CROSS-REFERENCE TO RELATED APPLICATIONS

The present application is a continuation of U.S. application Ser. No. 14/067,713, filed Oct. 30, 2013, now U.S. Pat. No. 10,335,034, which claims priority to U.S. Provisional Application No. 61/720,816, filed Oct. 31, 2012, the entireties of which are incorporated herein by reference.

TECHNICAL FIELD

Embodiments of the present disclosure relate generally to the field of medical devices and, more particularly, to dependency-based startup in a multi-modality medical system.

BACKGROUND

Innovations in diagnosing and verifying the level of success of treatment of disease have migrated from external imaging processes to internal diagnostic processes. In particular, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include angiography, intravascular ultrasound (IVUS), forward looking IVUS (FL-IVUS), fractional flow reserve (FFR) determination, a coronary flow reserve (CFR) determination, optical coherence tomography (OCT), trans-esophageal echocardiography, and image-guided therapy. Each of these techniques may be better suited for different diagnostic situations. To increase the chance of successful treatment, health care facilities may have a multitude of imaging, treatment, diagnostic, and sensing modalities on hand in a catheter lab during a procedure. Recently, processing systems have been designed that collect medical data from a plurality of different imaging, treatment, diagnostic, and sensing tools and process the multi-modality medical data. Such multi-component systems often include modules that depend on each other for information and system services. For example, two different modules may rely on a common error handling module to log errors in a log file. Often, such interdependent components need to be started in a specific order to function properly. Traditionally, designers of such multi-component medical processing systems have manually derived a correct startup sequence and then hard-coded the derived sequence into the system. Such a methodology would need to be repeated every time a component is added or removed from a multi-component system. Further, current integrated software solutions that combine multiple imaging modalities are difficult to upgrade and are otherwise problematic.

Accordingly, while the existing medical processing devices and methods have been generally adequate for their intended purposes, they have not been entirely satisfactory in all respects.

SUMMARY

The present disclosure is directed to methods and systems for initializing a medical processing system that handles medical data associated with multiple different modalities. During initialization of the medical processing system, different components corresponding to the different medical modalities are started in a specific order based upon dependencies between them. The start order is derived from a dependency map generated from dependency information associated with the components.

In one exemplary aspect, the present disclosure is directed to a dependency-based startup method in a multi-modality medical processing system. The method includes receiving initialization information about a plurality of executable components to be started during a startup sequence of the multi-modality medical processing system, the plurality of executable components including an executable modality component configured to communicate with a medical device communicatively coupled to the multi-modality medical processing system. The method also includes receiving dependency information about the executable modality component, the dependency information identifying one or more of the executable components upon which the executable modality component depends and transforming the initialization information and the dependency information into a dependency map that represents the dependencies between the plurality of executable components. Further, the method includes deriving a start order for the plurality of executable components based on the dependency map, wherein the one or more executable components upon which the executable modality component depends come before the executable modality component in the start order and starting the plurality of executable components in the multi-modality medical processing system according to the start order.

In another exemplary aspect, the present disclosure is directed to a multi-modality medical system including a computing system communicatively coupled to a medical device. The computing system includes a plurality of executable components to be started during a startup sequence of the computing system, the plurality of executable components including an executable modality component configured to receive medical data from the medical device. The computing system also includes a system controller configured to receive initialization information and dependency information about the plurality of executable components, the dependency information identifying one or more of the executable components upon which the executable modality component depends and build a dependency map based on the initialization information and the dependency information, the dependency map representing the dependencies between the plurality of executable components. The system controller is also configured to derive a start order for the plurality of executable components based on the dependency map, wherein the one or more executable components upon which the executable modality component depends come before the executable modality component in the start order and start the plurality of executable components of the computing system according to the start order.

In yet another exemplary aspect, the present disclosure is directed to a method of initializing a multi-modality medical processing system. The method includes receiving initialization information about first, second, and third executable components to be started during a startup sequence of the multi-modality medical processing system, the first executable component being configured to receive medical data associated with a first medical modality from a first medical device communicatively coupled to the multi-modality processing system, and the second executable component being configured to receive medical data associated with a second medical modality different than the first medical modality from a second medical device communicatively coupled to the multi-modality medical processing system. The method also includes receiving dependency information about the first, second, and third executable components, the dependency information indicating that the first and second executable components depend upon the third executable component and transforming the initialization information and the dependency information into a dependency map representing the dependencies between the first, second, and third executable components. Further, the method includes deriving a start order for the first, second, and third executable components based on the dependency map, wherein the third executable component comes before the first and second executable components in the start order and starting the first, second, and third executable components of the multi-modality medical processing system according to the start order.

DETAILED DESCRIPTION

Figure 1:
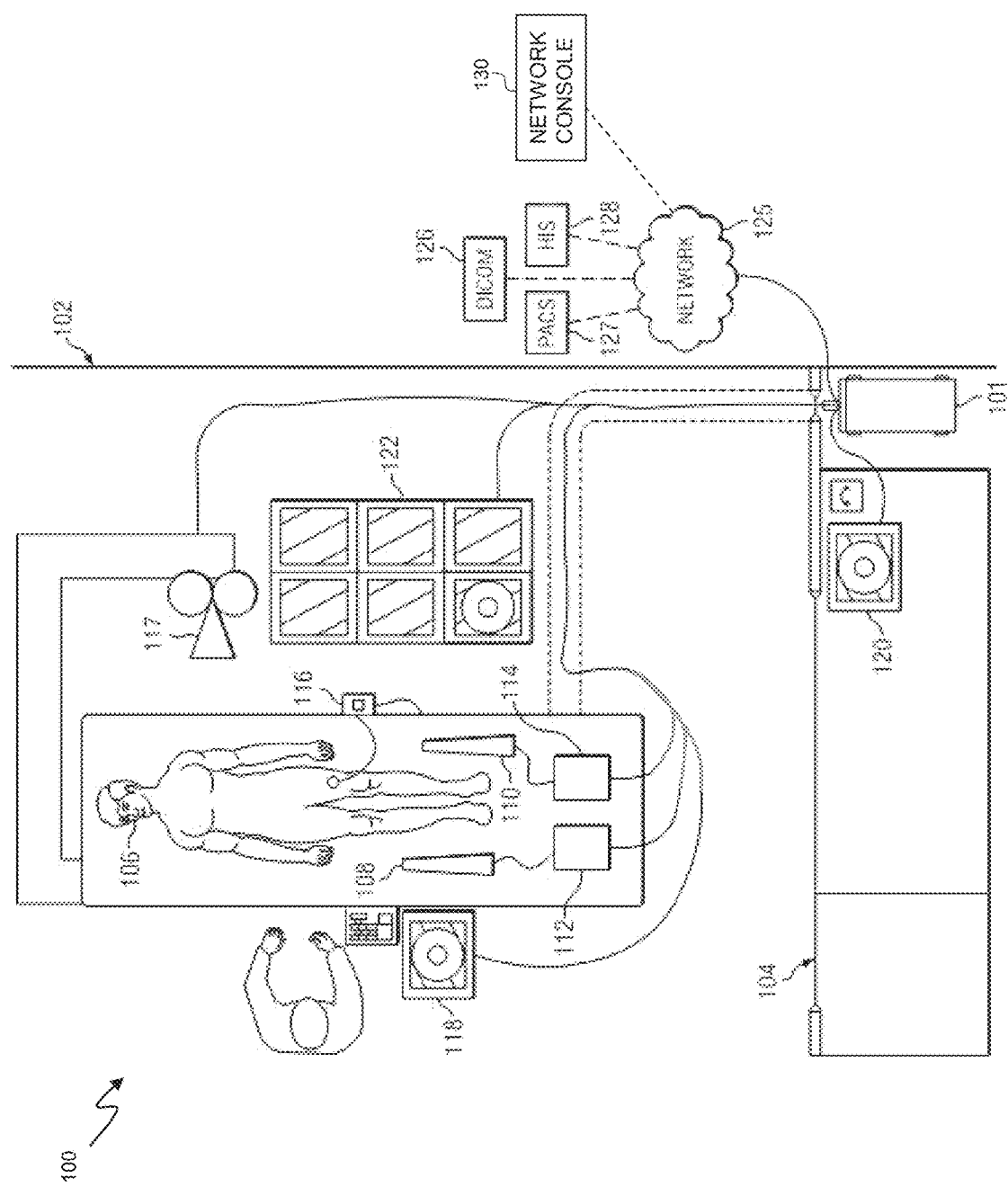
FIG. 1 is a schematic drawing depicting a medical system including a multi-modality processing system according to one embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic drawing depicting a medical system 100 including a multi-modality processing system 101 according to one embodiment of the present disclosure. In general, the medical system 100 provides for coherent integration and consolidation of multiple forms of acquisition and processing elements designed to be sensitive to a variety of methods used to acquire and interpret human biological physiology and morphological information and coordinate treatment of various conditions. More specifically, in system 100, the multi-modality processing system 101 is an integrated device for the acquisition, control, interpretation, and display of multi-modality medical sensing data. In one embodiment, the processing system 101 is a computer system with the hardware and software to acquire, process, and display multi-modality medical data, but, in other embodiments, the processing system 101 may be any other type of computing system operable to process medical data. In the embodiments in which processing system 101 is a computer workstation, the system includes at least a processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and a network communication device such as an Ethernet controller or wireless communication controller. In that regard, in some particular instances the processing system 101 is programmed to execute steps associated with the data acquisition and analysis described herein. Accordingly, it is understood that any steps related to data acquisition, data processing, instrument control, and/or other processing or control aspects of the present disclosure may be implemented by the processing system using corresponding instructions stored on or in a non-transitory computer readable medium accessible by the processing system. In some instances, the processing system 101 is portable (e.g., handheld, on a rolling cart, etc.). Further, it is understood that in some instances processing system 101 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

In the illustrated embodiment, the medical system 100 is deployed in a catheter lab 102 having a control room 104, with the processing system 101 being located in the control room. In other embodiments, the processing system 101 may be located elsewhere, such as in the catheter lab 102, in a centralized area in a medical facility, or at an off-site location (i.e., in the cloud). The catheter lab 102 includes a sterile field generally encompassing a procedure area but its associated control room 104 may or may not be sterile depending on the requirements of a procedure and/or health care facility. The catheter lab and control room may be used to perform on a patient any number of medical sensing procedures such as angiography, intravascular ultrasound (IVUS), virtual histology (VH), forward looking IVUS (FL-IVUS), intravascular photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intravascular palpography, transesophageal ultrasound, or any other medical sensing modalities known in the art. Further, the catheter lab and control room may be used to perform one or more treatment or therapy procedures on a patient such as radiofrequency ablation (RFA), cryotherapy, atherectomy or any other medical treatment procedure known in the art. For example, in catheter lab 102 a patient 106 may be undergoing a multi-modality procedure either as a single procedure or in combination with one or more sensing procedures. In any case, the catheter lab 102 includes a plurality of medical instruments including medical sensing devices that may collect medical sensing data in various different medical sensing modalities from the patient 106.

In the illustrated embodiment of FIG. 1, instruments 108 and 110 are medical sensing devices that may be utilized by a clinician to acquire medical sensing data about the patient 106. In a particular instance, the device 108 collects medical sensing data in one modality and the device 110 collects medical sensing data in a different modality. For instance, the instruments may each collect one of pressure, flow (velocity), images (including images obtained using ultrasound (e.g., IVUS), OCT, thermal, and/or other imaging techniques), temperature, and/or combinations thereof. The devices 108 and 110 may be any form of device, instrument, or probe sized and shaped to be positioned within a vessel, attached to an exterior of the patient, or scanned across a patient at a distance.

In the illustrated embodiment of FIG. 1, instrument 108 is an IVUS catheter 108 that may include one or more sensors such as a phased-array transducer to collect IVUS sensing data. In some embodiments, the IVUS catheter 108 may be capable of multi-modality sensing such as IVUS and IVPA sensing. Further, in the illustrated embodiment, the instrument 110 is an OCT catheter 110 that may include one or more optical sensors configured to collect OCT sensing data. In some instances, an IVUS patient interface module (PIM) 112 and an OCT PIM 114 respectively couple the IVUS catheter 108 and OCT catheter 110 to the medical system 100. In particular, the IVUS PIM 112 and the OCT PIM 114 are operable to respectively receive medical sensing data collected from the patient 106 by the IVUS catheter 108 and OCT catheter 110 and are operable to transmit the received data to the processing system 101 in the control room 104. In one embodiment, the PIMs 112 and 114 include analog to digital (A/D) converters and transmit digital data to the processing system 101, however, in other embodiments, the PIMs transmit analog data to the processing system. In one embodiment, the IVUS PIM 112 and OCT PIM 114 transmit the medical sensing data over a Peripheral Component Interconnect Express (PCIe) data bus connection, but, in other embodiments, they may transmit data over a USB connection, a Thunderbolt connection, a FireWire connection, or some other high-speed data bus connection. In other instances, the PIMs may be connected to the processing system 101 via wireless connections using IEEE 802.11 Wi-Fi standards, Ultra Wide-Band (UWB) standards, wireless FireWire, wireless USB, or another high-speed wireless networking standard.

Additionally, in the medical system 100, an electrocardiogram (ECG) device 116 is operable to transmit electrocardiogram signals or other hemodynamic data from patient 106 to the processing system 101. In some embodiments, the processing system 101 may be operable to synchronize data collected with the catheters 108 and 110 using ECG signals from the ECG 116. Further, an angiogram system 117 is operable to collect x-ray, computed tomography (CT), or magnetic resonance images (MRI) of the patient 106 and transmit them to the processing system 101. In one embodiment, the angiogram system 117 may be communicatively coupled to the processing system to the processing system 101 through an adapter device. Such an adaptor device may transform data from a proprietary third-party format into a format usable by the processing system 101. In some embodiments, the processing system 101 may be operable to co-register image data from angiogram system 117 (e.g., x-ray data, Mill data, CT data, etc.) with sensing data from the IVUS and OCT catheters 108 and 110. As one aspect of this, the co-registration may be performed to generate three-dimensional images with the sensing data.

A bedside controller 118 is also communicatively coupled to the processing system 101 and provides user control of the particular medical modality (or modalities) being used to diagnose the patient 106. In the current embodiment, the bedside controller 118 is a touch screen controller that provides user controls and diagnostic images on a single surface. In alternative embodiments, however, the bedside controller 118 may include both a non-interactive display and separate controls such as physical buttons and/or a joystick. In the integrated medical system 100, the bedside controller 118 is operable to present workflow control options and patient image data in graphical user interfaces (GUIs). As will be described in greater detail in association with FIG. 2, the bedside controller 118 includes a user interface (UI) framework service through which workflows associated with multiple modalities may execute. Thus, the bedside controller 118 is capable displaying workflows and diagnostic images for multiple modalities allowing a clinician to control the acquisition of multi-modality medical sensing data with a single interface device.

A main controller 120 in the control room 104 is also communicatively coupled to the processing system 101 and, as shown in FIG. 1, is adjacent to catheter lab 102. In the current embodiment, the main controller 120 is similar to the bedside controller 118 in that it includes a touch screen and is operable to display multitude of GUI-based workflows corresponding to different medical sensing modalities via a UI framework service executing thereon. In some embodiments, the main controller 120 may be used to simultaneously carry out a different aspect of a procedure's workflow than the bedside controller 118. In alternative embodiments, the main controller 120 may include a non-interactive display and standalone controls such as a mouse and keyboard.

The medical system 100 further includes a boom display 122 communicatively coupled to the processing system 101. The boom display 122 may include an array of monitors, each capable of displaying different information associated with a medical sensing procedure. For example, during an IVUS procedure, one monitor in the boom display 122 may display a tomographic view and one monitor may display a sagittal view.

Further, the multi-modality processing system 101 is communicatively coupled to a data network 125. In the illustrated embodiment, the data network 125 is a TCP/IP-based local area network (LAN), however, in other embodiments, it may utilize a different protocol such as Synchronous Optical Networking (SONET), or may be a wide area network (WAN). The processing system 101 may connect to various resources via the network 125. For example, the processing system 101 may communicate with a Digital Imaging and Communications in Medicine (DICOM) system 126, a Picture Archiving and Communication System (PACS) 127, and a Hospital Information System (HIS) 128 through the network 125. Additionally, in some embodiments, a network console 130 may communicate with the multi-modality processing system 101 via the network 125 to allow a doctor or other health professional to access the aspects of the medical system 100 remotely. For instance, a user of the network console 130 may access patient medical data such as diagnostic images collected by multi-modality processing system 101, or, in some embodiments, may monitor or control one or more on-going procedures in the catheter lab 102 in real-time. The network console 130 may be any sort of computing device with a network connection such as a PC, laptop, smartphone, tablet computer, or other such device located inside or outside of a health care facility.

Additionally, in the illustrated embodiment, medical sensing tools in system 100 discussed above are shown as communicatively coupled to the processing system 101 via a wired connection such as a standard copper link or a fiber optic link, but, in alternative embodiments, the tools may be connected to the processing system 101 via wireless connections using IEEE 802.11 Wi-Fi standards, Ultra Wide-Band (UWB) standards, wireless FireWire, wireless USB, or another high-speed wireless networking standard.

One of ordinary skill in the art would recognize that the medical system 100 described above is simply an example embodiment of a system that is operable to collect diagnostic data associated with a plurality of medical modalities. In alternative embodiments, different and/or additional tools may be communicatively coupled to the processing system 101 so as to contribute additional and/or different functionality to the medical system 100.

Figure 2:
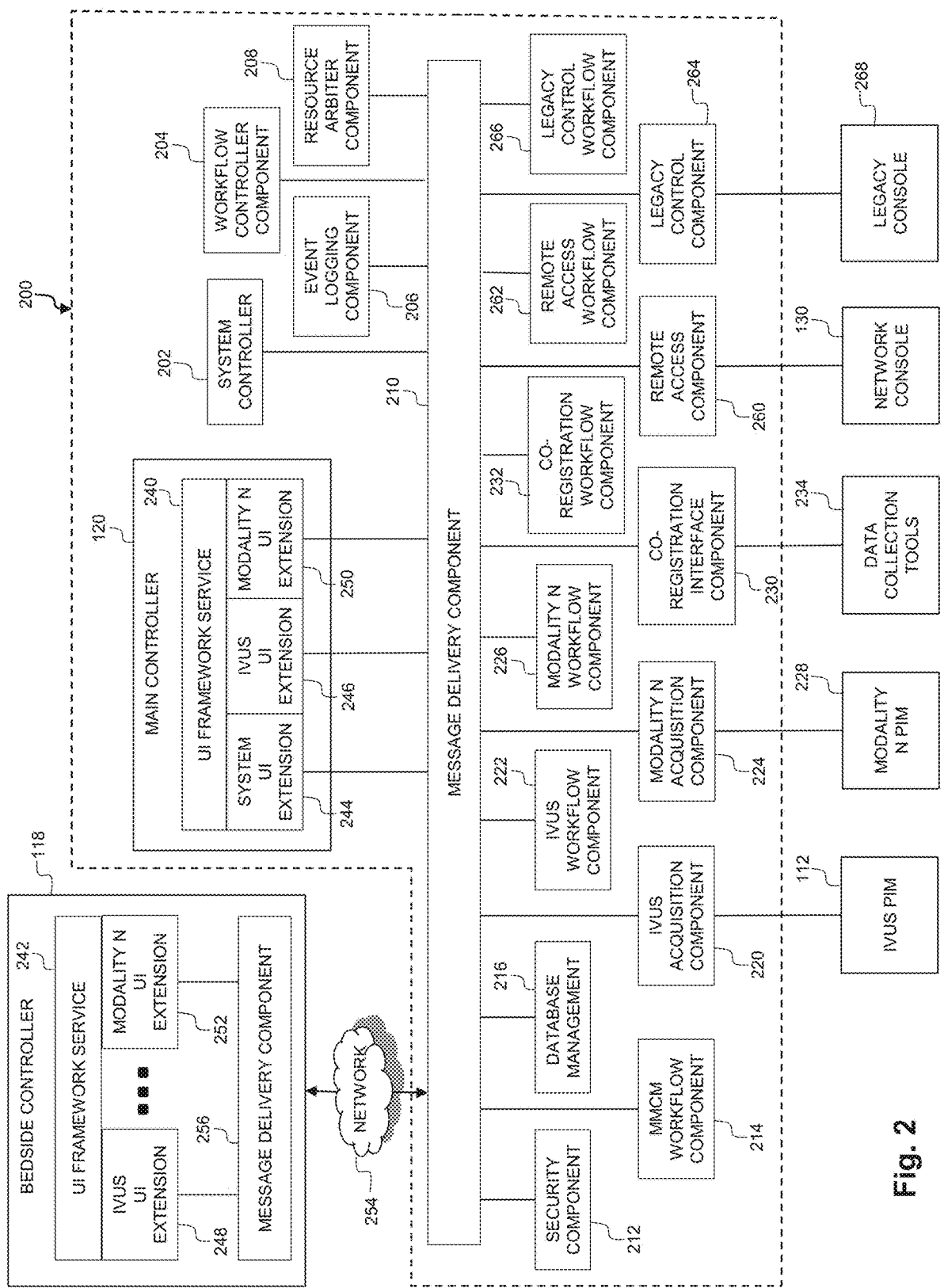
FIG. 2 is a functional block diagram of portions of the medical system, including a processing framework executing on an embodiment of the multi-modality processing system.

With reference now to FIG. 2, illustrated is a functional block diagram of portions of the medical system 100, including a processing framework 200 executing on an embodiment of the multi-modality processing system 101. The processing framework 200 includes various independent and dependent executable components that control the operation of the processing system 101, including the acquisition, processing, and display of multi-modality medical sensing data. In general, the processing framework 200 of processing system 101 is modular and extensible. That is, the framework 200 is comprised of independent software and/or hardware components (or extensions) respectively associated with different functions and medical sensing modalities. This modular design allows the framework to be extended to accommodate additional medical sensing modalities and functionality without impacting existing functionality or requiring changes to the underlying architecture. Further, an internal messaging system facilitates independent data communication between modules within the framework. In one instance, the processing framework 200 may be implemented as computer-executable instructions stored on a non-transitory computer-readable storage medium in the processing system 10. In other instances the processing framework 200 may be a combination of hardware and software modules executing within with the processing system 101.

Generally, in the embodiment shown in FIG. 2, processing framework 200 includes a plurality of components that are configured to receive medical sensing data from a plurality of medical sensing devices, process the data, and output the data as diagnostic images via the main controller 120, the bedside controller 118, or other graphical display device. The framework 200 includes several system-level components that manage the core system functions of the processing system 101 and also coordinate the plurality of modality-specific components. For instance, the framework 200 includes a system controller 202 that coordinates startup and shutdown of the plurality of executable components of the processing framework 200, including hardware and software modules related to acquisition and processing of patient diagnostic data. The system controller 202 is also configured to monitor the state of components executing within the framework 202, for instance, to determine if any components have unexpectedly stopped executing. In addition, the system controller 202 provides an interface through which other framework components may obtain system configuration and status information. Because the software framework 200 is modular, the system controller 202 is independent of the components within the framework that it manages so that errors and changes made to components do not affect the execution or structure of the system controller. The manner in which the system controller 202 starts and stops the executable components of the framework 202 will be described in greater detail in FIGS. 3-5.

As mentioned above, the framework 200 is configured such that various extensions may be added and removed without system architecture changes. In certain embodiments, an extension executing within framework 200 may include a plurality of executable components that together implement the full functionality of the extension. In such embodiments, an extension may include an extension controller that is similar to the system controller 202 that is operable to startup, shutdown, and monitor the various executable components associated with the extension. For example, upon system startup, the system controller 202 may start an extension controller corresponding to a medical modality, and then the extension controller may, in turn, start the executable components associated with the modality. In one embodiment, extension controllers may be unallocated until system controller 202 associates them with a specific modality or other system task via parameters retrieved from a configuration mechanism, such as a configuration file.

The processing framework 200 further includes a workflow controller component 204 that is generally configured to govern the execution of the executable components of the framework 202 during multi-modality medical sensing workflows. The workflow controller component 204 may govern workflows executed by the processing framework 200 in various different manners.

The processing framework 200 further includes an event logging component 206 that is configured to log messages received from various components of the processing framework. For instance, during system startup, the system controller 202 may send messages about the status of components being started to the event logging component 206 which, in turn, writes the messages to a log file in a standardized format. Additionally, the processing framework 200 includes a resource arbiter component 208 that is configured to manage the sharing of limited system resources between various executable components of the framework 202 during multi-modality medical sensing and/or treatment workflows. For example, during a multi-modality workflow, two or more components associated with different modalities within the processing framework 202 may be vying for the same system resource such as a graphical display on the main controller 120. The resource arbiter component 208 may coordinate sharing of limited system resources in various manners such as through a lock system, a queue system, or a hierarchical collision management system.

In one embodiment, the system controller 202, workflow controller component 204, event logging component 206, and resource arbiter component 208 may be implemented as processor-executable software stored on non-transitory, computer-readable storage medium, but in alternative embodiments, these components may be implemented as hardware components such as special purpose microprocessors, Field Programmable Gate Arrays (FPGAs), microcontrollers, graphics processing units (GPU), digital signal processors (DSP). Alternatively, the components of the processing framework may be implemented as a combination of hardware and software. In certain embodiments in which executable components are implemented in FPGAs, the system controller 202 may be configured to dynamically alter the programmable logic within the FPGAs to implement various functionality needed at the time. As an aspect of this, the processing system 101 may include one or more unassigned FPGAs that may be allocated by the system controller during system startup. For instance, if upon startup of the processing system 101, the system controller detects an OCT PIM and catheter coupled thereto, the system controller or an extension controller associated with OCT functionality may dynamically transform the programmable logic within one the unassigned FPGAs such that it includes functionality to receive and/or process OCT medical data.

To facilitate intersystem communication between different hardware and software components in the multi-modality processing system 101, the processing framework 200 further includes a message delivery component 210. In one embodiment, the message delivery component 210 is configured to receive messages from components within the framework 202, determine the intended target of the messages, and deliver the messages in timely manner (i.e., the message delivery component is an active participant in the delivery of messages). In such an embodiment, message metadata may be generated by the sending component that includes destination information, payload data (e.g., modality type, patient data, etc.), priority information, timing information, or other such information. In another embodiment, message delivery component 210 may be configured to receive messages from components within the framework 202, temporarily store the messages, and make the messages available for retrieval by other components within the framework (i.e., the message delivery component is a passive queue). In any case, the message delivery component 210 facilitates communication between executable components in the framework 200. For instance, the system controller 202 may utilize the message delivery component 210 to inquire into the status of components starting up during a system startup sequence, and then, upon the receiving status information, utilize the message delivery component to transmit the status information to the event logging component 206 so that it may be written to a log file. Similarly, the resource arbiter component 208 may utilize the message delivery component 210 to pass a resource token between components requesting access to limited resources.

In one example embodiment in which the message delivery component 210 is a passive queue, components in the framework 200 may packetize incoming medical sensing data into messages and then transmit the messages to a queue on the message delivery component where they may be retrieved by other components such as image data processing components. Further, in some embodiments, the message delivery component 210 is operable to make received messages available in a First-In-First-Out (FIFO) manner, wherein messages that arrive on the queue first will be removed from the queue first. In alternative embodiments, the message delivery component 210 may make messages available in a different manner for instance by a priority value stored in a message header. In one embodiment, the message delivery component 210 is implemented in random-access memory (RAM) in the processing system 101, but, in other embodiments, it may be implemented in non-volatile RAM (NVRAM), secondary storage (e.g., magnetic hard drives, flash memory, etc.), or network-based storage. Further, in one embodiment, messages stored on the message delivery component 210 may be accessed by software and hardware modules in processing system 101 using Direct Memory Access (DMA).

The processing framework 202 further includes a number of additional system components that provide core system functionality including a security component 212, a multi-modality case management (MMCM) component 214, and a database management component 216. In certain embodiments, the security component 212 is configured to provide various security services to the overall processing framework and to individual components. For example, components implementing an IVUS data acquisition workflow may utilize encryption application programming interfaces (APIs) exposed by the security component 212 to encrypt IVUS data before it is transmitted over a network connection. Further, the security component 212 may provide other security services, such as system-level authentication and authorization services to restrict access to the processing framework to credentialed users and also to prevent the execution of untrusted components within the extensible framework. The multi-modality case management (MMCM) component 214 is configured to coordinate and consolidate diagnostic data associated with a plurality of medical modalities into a unified patient record that may be more easily managed. Such a unified patient record may be more efficiently stored in a database and may be more amenable to data archival and retrieval. In that regard, the database management component 216 is configured to present transparent database services to the other components in the framework 200 such that database connection and management details are hidden from the other components. For example, in certain embodiments, the database management component 216 may expose an API that includes database storage and retrieval functionality to components of the framework 200. In other words, a medical sensing workflow component may be able to transmit diagnostic data to a local and/or remote database such as a DICOM or PACS server via the database component without being aware of database connection details. In other embodiments, the database management component 216 may be operable perform additional and/or different database services such as data formatting services that prepare diagnostic data for database archival.

As mentioned above, the processing framework 200 of the multi-modality processing system 101 is operable to receive and process medical data associated with a plurality of modalities. In that regard, the processing framework 200 includes a plurality of modular acquisition components and workflow components that are respectively associated with different medical sensing and diagnostic modalities. For instance, as shown in the illustrated embodiment of FIG. 2, the processing framework 200 includes an IVUS acquisition component 220 and an IVUS workflow component 222 that are respectively configured to receive and process IVUS medical sensing data from the IVUS PIM 112. In accordance with the modular and extensible nature of the processing framework 200, any number of additional acquisition and workflow components may be independently added to the framework as denoted by the modality "N" acquisition component 224 and the modality "N" workflow component 226 that acquire and process data from a modality "N" PIM 228. For example, in certain embodiments, the processing system 101 may be communicatively coupled to the OCT PIM 114, the ECG system 116, a fractional flow reserve (FFR) PIM, a FLIVUS PIM, and an ICE PIM. In other embodiments, additional and/or different medical sensing, treatment, or diagnostic devices may be coupled to the processing system 101 via additional and/or different data communication connections known in the art. In such a scenario, in addition to the IVUS acquisition module 220, the processing framework 200 may include an FFR acquisition component to receive FFR data from an FFR PIM, a FLIVUS acquisition component to receive FLIVUS data from a FLIVUS PIM, an ICE acquisition component to receive ICE data from an ICE PIM, and an OCT acquisition component is operable to receive OCT data from an OCT PIM. In this context, medical data communicated between the executable components of the processing framework 200 and the communicatively coupled medical devices (e.g., PIMs, catheters, etc.) may include data collected by sensors, control signals, power levels, device feedback, and other medical data related to a sensing, treatment, or diagnostic procedure. Further, in certain embodiments, patient treatment devices may be communicatively coupled to the processing system 101 such as devices associated with radiofrequency ablation (RFA), cryotherapy, or atherectomy and any PIMs or other control equipment associated with such treatment procedures. In such an embodiment, the modality "N" acquisition component 224 and the modality "N" workflow component 226 may be configured to communicate with and control the treatment devices such as by relaying control signals, relaying power levels, receiving device feedback, and receiving data collected by sensors disposed on the treatment devices.

In one embodiment, once the acquisition components 220 and 224 have received data from connected medical sensing devices, the components packetize the data into messages to facilitate intersystem communication. Specifically, the components may be operable to create a plurality of messages from an incoming digital data stream, where each message contains a portion of the digitized medical sensing data and a header. The message header contains metadata associated with the medical sensing data contained within the message. Further, in some embodiments, the acquisition components 220 and 224 may be operable to manipulate the digitized medical sensing data in some way before it is transmitted to other portions of the framework 200. For example, the acquisition components may compress the sensing data to make intersystem communication more efficient, or normalize, scale or otherwise filter the data to aid later processing of the data. In some embodiments, this manipulation may be modality-specific. For example, the IVUS acquisition component 220 may identify and discard redundant IVUS data before it is passed on to save processing time in subsequent steps. The acquisition components 220 and 224 may additionally perform a number of tasks related to the acquisition of data including responding to interrupts generated by data buses (e.g., PCIe, USB), detecting which medical sensing devices are connected to processing system 101, retrieving information about connected medical sensing devices, storing sensing device-specific data, and allocating resources to the data buses. As mentioned above, the data acquisition components are independent from each other and may be installed or removed without disrupting data acquisition by other components. Additionally, acquisition components are independent of underlying data bus software layers (for example, through the use of APIs) and thus may be created by third parties to facilitate acquisition of data from third party medical sensing devices.

The workflow components of the processing framework, such as the IVUS workflow component 222, receive unprocessed medical sensing and/or diagnostic data from respective acquisition components via the message delivery component 210. In general, the workflow components are configured to control the acquisition of medical sensing data such as by starting and stopping data collection at calculated times, displaying acquired and processed patient data, and facilitating the analysis of acquired patient data by a clinician. As an aspect of this, the workflow components are operable to transform unprocessed medical data gathered from a patient into diagnostic images or other data formats that enable a clinician to evaluate a patient's condition. For example, an IVUS workflow component 222 may interpret IVUS data received from the IVUS PIM 112 and convert the data into human-readable IVUS images. In one embodiment, a software stack within the framework may expose a set of APIs with which the workflow component 222 and other workflow components in the framework may call to access system resources such as the computational resources, the message delivery component 210, and communication resources. After processing acquired data, the modality-centric workflow components may transmit one or messages containing the processed data to other components within the framework 200 via the message delivery component 210. In some embodiments, before sending such messages, the components may insert a flag in the header indicating that the message contains processed data. Additionally, in some embodiments, after processing medical sensing data, the components may utilize the database management component 216 to transmit the processed data to archival systems such as a locally attached mass storage device or the network-based PACS server 127. In accordance with the modular architecture of the processing framework 200, the workflow components 222 and 226 are independent of each other and may be installed or removed without disrupting other components, and may be written by third parties. Further, due to their independence, they may be are operable to process signaling and imaging data from multiple medical sensing devices concurrently.

The processing framework 200 additionally includes a co-registration interface component 230 and a co-registration workflow component 232 that are configured to acquire and process data from any number of data collection tools 234 and co-register the acquired data with data acquired by one of the other acquisition components within the framework. In more detail, the co-registration interface component 230 may be operable to communicatively interface with medical data acquisition tools associated with any number of modalities, such as the ECG device 116 or the angiography system 117 of FIG. 1. In certain embodiments, the interface component 230 may be operable to standardize and/or transform incoming modality data such that it may be co-registered with other sensing data acquired by the processing system 101. As medical data is being acquired by the co-registration interface component 230, the co-registration workflow component 232 is configured to facilitate the co-registration of data from different modalities such as by spatially or temporally synchronizing data collection among medical sensing devices, aligning two or more acquired data sets based on spatial or temporal registration markers, and generating co-registered diagnostic images or other human-readable data that enable a clinician to evaluate a patient's condition. Further, in other embodiments, the co-registration workflow component 232 may be operable to spatially co-register catheter-gathered data in a two-dimensional (2-D) or three-dimensional (3-D) space using previously-generated 2-D images or 3-D models. For example, a catheter-based sensing tool may include fiducials that are tracked to generate position data during a sensing procedure, and the co-registration workflow component 232 may register this position data against previously acquired MRI data. Still further, the co-registration workflow component 232 may facilitate co-registration of multi-modality data acquired by native acquisition components within the framework 200 such as the IVUS acquisition component 220 and modality "N" acquisition component 224. Additionally, in some embodiments, a real-time clock may be integrated into the co-registration workflow component 232. U.S. Provisional Patent Application No. 61/473,591, entitled "DISTRIBUTED MEDICAL SENSING SYSTEM AND METHOD", discloses temporally synchronizing medical sensing data collection in more detail and is hereby incorporated by reference in its entirety.

As discussed above in association with FIG. 1, a clinician utilizing the processing system 101 may control workflows and view diagnostic images through the main controller 120 and the bedside controller 118. The main controller 120 and the bedside controller 118 respectively include user interface (UI) framework services 240 and 242 that support a plurality of user interface (UI) extensions (or components). In general, the UI extensions supported by the UI framework services 240 and 242 respectively correspond to medical sensing modalities and are operable to render a user interface for control of the associated acquisition workflow and display of processed sensing data. Similar to the processing framework 200, the UI frameworks 240 and 242 are extensible in that they support UI extensions that are independent of one another. That is, its modular design allows the UI frameworks 240 and 242 to be extended to accommodate additional medical sensing modality user interfaces without impacting existing user interfaces or requiring changes to the underlying UI architectures. In the illustrated embodiment, the main controller 120 includes a system UI extension 244 that renders a user interface containing core system controls and configuration options. For example, a clinician may startup, shutdown or otherwise manage the processing system 101 using the user interface rendered by the system UI extension 244. In one embodiment, the components of the main controller 120 may be considered part of the processing framework 200. The IVUS UI extensions 246 and 248 render user interfaces for the main controller 120 and bedside controller 118, respectively. For example, the IVUS UI extensions 246 and 248 may render and display the touch screen buttons used to control an IVUS workflow and also render and display the IVUS diagnostic images created by the IVUS workflow component 222. Similarly, the modality "N" UI extensions 250 and 252 render controls and images associated with a modality "N" workflow.

In one embodiment, the UI framework services 240 and 242 may expose APIs with which the UI extensions may call to access system resources such as a look-and-feel toolbox and error handling resources. Look-and-feel toolbox APIs enable the UI extensions to present a standardized user interface with common buttons, parallel workflow formats, and data presentation schemes for different modality workflows. In this manner, clinicians may more easily transition between acquisition modalities without additional user interface training. Further, co-registration UI extensions may present and/or combine processed image or signaling data from multiple modalities. For instance, a UI extension may display an electrocardiogram (ECG) wave adjacent to IVUS imaging data or may display an IVUS image overlaid with borders that were previously drawn on an OCT image. Further, in some embodiments, the UI framework services 240 and 242 may include a multi-tasking framework to coordinate concurrently executing UI extensions. For instance, in the event the processing system 101 is simultaneously acquiring data associated with more than one modality, the UI framework services 240 and 242 may present the user with a modality selector screen on which a desired user interface may be selected.

The UI framework service 240 communicates with the components of the processing framework 200 via the message delivery component 210. As shown in the illustrated embodiment of FIG. 2, the bedside controller 118 may be communicatively coupled to the processing framework 200 via a network connection 254. The network connection 254 may be any type of wired of wireless network connection such as an Ethernet connection or IEEE 802.11 Wi-Fi connection. Alternatively, one or both of the main and bedside controllers 120 and 118 may communicate with the processing framework 200 via a local bus connection such as a (PCIe) data bus connection, a USB connection, a Thunderbolt connection, a FireWire connection, or some other high-speed data bus connection. Further, in the illustrated embodiment of FIG. 2, the bedside controller includes a message delivery component 256 that is configured to facilitate message-based communication between the UI extensions in the bedside controller 118 and the components in the processing framework 200. In certain embodiments, the message delivery component 256 may extract diagnostic image data from network communication packets as they arrive over the network connection 254.

The processing framework 200 includes additional components that allow a clinician to access and/or control workflows executing in the multi-modality processing system 101. For example, the framework 200 includes a remote access component 260 that communicatively couples the network console 130 (FIG. 1) to the processing framework 200. In one embodiment, the remote access component 260 is operable to export control functionality of the processing system 101 to the network console 130, so that the network console may present workflow control functions in its user interface. In certain embodiments, the remote access component 260 may receive workflow commands from the network console 130 and forward them to a remote access workflow component 262. The remote access workflow component 262 may dictate the set of commands and diagnostic data to which a remote user may access through the network console 130. Further, the legacy control component 264 and legacy control workflow component 266 provide some level of access to modality workflow control and data to users of legacy consoles 268 (e.g. button consoles, mice, keyboards, standalone monitors).

In one embodiment, the core system components of the processing framework 200 and the additional components such as the modality-related components may be implemented as processor-executable software stored on non-transitory, computer-readable storage medium, but in alternative embodiments, these components may be implemented as hardware components such as special purpose microprocessors, Field Programmable Gate Arrays (FPGAs), microcontrollers, graphics processing units (GPU), digital signal processors (DSP). Alternatively, the components of the processing framework may be implemented as a combination of hardware and software.

One of ordinary skill in the art will recognize that the processing framework 200 of FIG. 2 is simply an example embodiment and, in alternative embodiments, the framework may include different and/or additional components configured to carry out various medical sensing workflows. For instance, the processing framework 200 may further include executable components configured for the evaluation of a stenosis of a human blood vessel or configured to facilitate control of computer-assisted surgery or remotely-controlled surgery.

Figure 3:
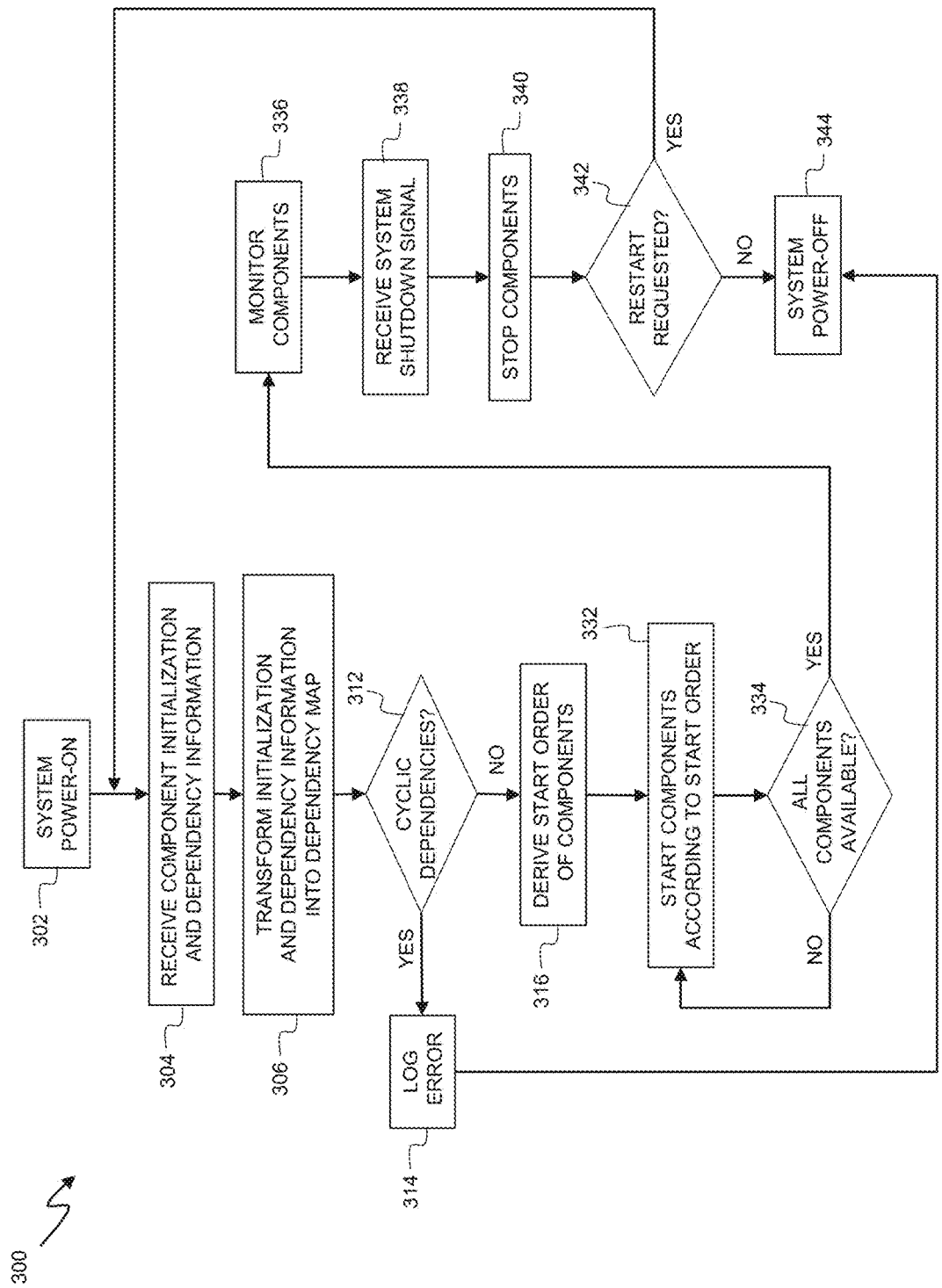
FIG. 3 is a high-level flowchart illustrating a method for a dependency-based startup sequence of a multi-modality processing system according to aspects of the present disclosure.

Referring now to FIG. 3, illustrated is a high-level flowchart illustrating a method 300 for a dependency-based startup sequence of a multi-modality medical processing system according to aspects of the present disclosure. In the illustrated embodiment, at least a portion of the method 300 is carried out by the system controller 202 of the processing framework 200 of FIG. 2. Further, in one embodiment, portions of the method 300 may be implemented as computer-readable instructions stored on a mass storage device or system memory and executed by a processor of the multi-modality processing system 101 of FIG. 1. Further, the method 300 in FIG. 3 is a high-level overview and details associated with various blocks in the method will be described in association with subsequent figures in the present disclosure.

The method 300 begins at block 302 where the processing system 101 is powered-on, restarted, or otherwise initialized. Once powered on, one or more hardware component verification tests may be performed by a Basic Input Output System (BIOS) or other low-level firmware interface in the processing system 101 to initialize the hardware components of the system. After hardware initialization, core system components of the processing framework 200, such as the system controller 202, are initialized. The system controller 202 is responsible for starting the remainder of the executable components associated with data acquisition, workflow management, and other medical data management in the processing framework 200. Many of these components rely upon one another for various services or functionality (i.e., they are interdependent), and thus, they must be started in a specific order so that services upon which other components rely are available when the components are started. For example, the security component 212 of the processing framework 200 may require the logging interfaces made available by the event logging component 206. Thus, the event logging component 206 should be started by the system controller 202 before the security component 212. According to aspects of the present disclosure, the system controller 202 is operable to dynamically derive a start order based upon the components' interdependencies and sequentially start the components so that each has access to all required interfaces when it is started to prevent deadlocks, boot loops, or other initialization errors.

In that regard, after the system controller 202 is initialized, method 300 proceeds to block 304 where the system controller receives component initialization and dependency information about the plurality of executable components that it is tasked with initializing during system startup. In one embodiment, the component initialization information associated with an executable component may include the component's name (i.e., its identifier), the name and file system location of the component's executable file, the command line arguments necessary to start the component with the executable file, the component type, component external interfaces, startup timeout, and recovery options. In alternative embodiments, additional and/or different information may be included in each component's initialization information such as priority information, memory allocation information, or hardware addressing information if an executable component is hardware-based. Dependency information associated with an executable component includes a list of other executable components upon which the executable component depends. In this context, a first executable component (i.e., a client) depends on a second executable component (i.e., a server) if the first utilizes functionality made available by interfaces exposed by the second. Thus, all of the second executable component's interfaces must be available before the first executable component can be properly started by the system controller. In alternative embodiments, additional and/or different information may be included in each component's dependency information such as the identities of the specific external interfaces upon which the component depends.

In one embodiment, the component initialization and dependency information is contained in a configuration file that is read by the system controller 202 upon system startup. At the least, such a configuration file includes a list of executable components to be started and, for each executable component in the list, the components upon which it depends. As a simple example, the configuration file may indicate that the event logging component 206, the workflow controller component 204, and the IVUS workflow component 222 need to be started by the system controller 202. Such a configuration file would also indicate that the IVUS workflow component 222 depends on both the event logging component 206 and the workflow controller component 204, and that the workflow controller component 204 depends on the event logging component 206. As will be described below, the system controller 202 is operable to take the information in such a configuration file and start the event logging component 206, the workflow controller component 204, and the IVUS workflow component 222 in the correct order based on the dependency information.

In certain embodiments, the configuration file read by the system controller 202 may be an Extensible Markup Language (XML) document with a defined schema. The following is a portion of an example XML configuration file that includes initialization information and dependency information for the event logging component 206, the workflow controller component 204, and the IVUS workflow component 222.

```
<ProgramObject version="1">
    <Name>EventLoggingComponent</Name>
    <Filename>c:\bin\EventLoggingComponent.exe</Filename>
    <CommandParameters></CommandParameters>
    <Synchronize timeout="30000">
        <SynchType>WaitForRegistration</SynchType>
    </Synchronize>
    <Recovery>ShutdownSystem</Recovery>
    <ProgramType>Logger</ProgramType>
    <Interface>i_executable</Interface>
</ProgramObject>
<ProgramObject version="1">
    <Name> WorkflowControllerComponent </Name>
    <Filename>c:\bin\ WorkflowControllerComponent.exe</Filename>
    <CommandParameters>WCCconfig.xml</CommandParameters>
    <Synchronize timeout="30000">
        <SynchType>WaitForRegistration</SynchType>
    </Synchronize>
    <Recovery>ShutdownSystem</Recovery>
    <ProgramType>CoreService</ProgramType>
    <Interface>i_executable</Interface>
</ProgramObject>
<ProgramObject version="1">
    <Name> IVUSWorkflowComponent </Name>
    <Filename>c:\ bin\ IVUSWorkflowComponent.exe</Filename>
    <CommandParameters>IVUSconfig.xml</CommandParameters>
    <Synchronize timeout="30000">
        <SynchType>WaitForPid</SynchType>
    </Synchronize>
    <Recovery>DisableModality</Recovery>
    <ProgramType>Modality</ProgramType>
    <Interface></Interface>
</ProgramObject>
<Dependency>
    <Client> IVUSWorkflowComponent </Client>
    <Server> WorkflowControllerComponent </Server>
    <Server> EventLoggingComponent </Server>
</Dependency>
<Dependency>
    <Client> WorkflowControllerComponent </Client>
    <Server> EventLoggingComponent </Server>
</Dependency>
```

As shown in the example XML configuration file portion above, initialization information for the IVUS workflow component 222 includes an identifier ("IVUSWorkflow-Component"), a filename of the executable to be started by the system controller ("c:\bin\IVUSWorkflowComponent.exe"), command parameters to be passed to the executable during command line execution ("IVUSconfig.xml"), a timeout and synchronization type, and recovery action to be taken in case of execution error ("Disable modality"). The XML configuration file also includes the dependency information for the IVUS workflow component 222 which lists the identifiers of the components upon which the IVUS workflow component depends (i.e., the WorkflowControllerComponent and EventLoggingComponent).

One of ordinary skill in the art would recognize that the above XML configuration file is simply an example and a configuration file for the framework 202 may include many more executable components and associated dependencies and may be formatted in any number of additional and/or different manners and contain additional and/or different information. Further, the system controller 202 may receive initialization and dependency information for executable components within processing framework 200 in various different manners besides reading a configuration file. For example, in one embodiment, the system controller 202 may retrieve configuration information from a centralized network configuration repository or a dedicated hardware memory device (e.g., an Electrically Erasable Programmable Read-Only Memory (EEPROM)). Further, the system controller may retrieve a combination of static and dynamic configuration information, for example, by reading a static configuration file listing core system components that are started during every startup sequence and also dynamically detecting which medical sensing devices are coupled to the processing system 101 and only starting the executable components associated with the detected medical sensing devices.

As mentioned above, the processing system 101 is operable to collect and process data associated with multiple medical modalities. Notably, if a particular modality is not needed during a particular medical procedure, the executable components related to the unneeded modality may be excluded from the list of executable components in the configuration information and thus will not be started by the system controller 202 during system startup. For instance, in one embodiment, if IVUS is not being performed on a patient during a catheter lab session, the IVUS acquisition module, the IVUS workflow component, and the IVUS UI extension may be excluded from the configuration file read by the system controller. In another embodiment, specific modalities or extensions may be excluded from startup with an exceptions file. Specifically, after the system controller 202 reads the configuration file, it may read an exceptions file that contains a list of executable components that should be temporarily deactivated. Such an exceptions file may also include expiration information that identifies a date after which an executable component should no longer be executed upon startup. Accordingly, by starting only the components needed for a specific procedure, the processing system 101 may operate in a more efficient manner and may avoid unnecessary errors related to unneeded executable components. Additionally, as mentioned previously, the processing framework 200 is extensible and thus executable components may be added that correspond to a new medical modality. In such a scenario, the new components may be installed into the process framework and their initialization and dependency information provided to the system controller at system startup. As such, the new modality components may be started without re-writing any existing system startup infrastructure.

Figure 4:
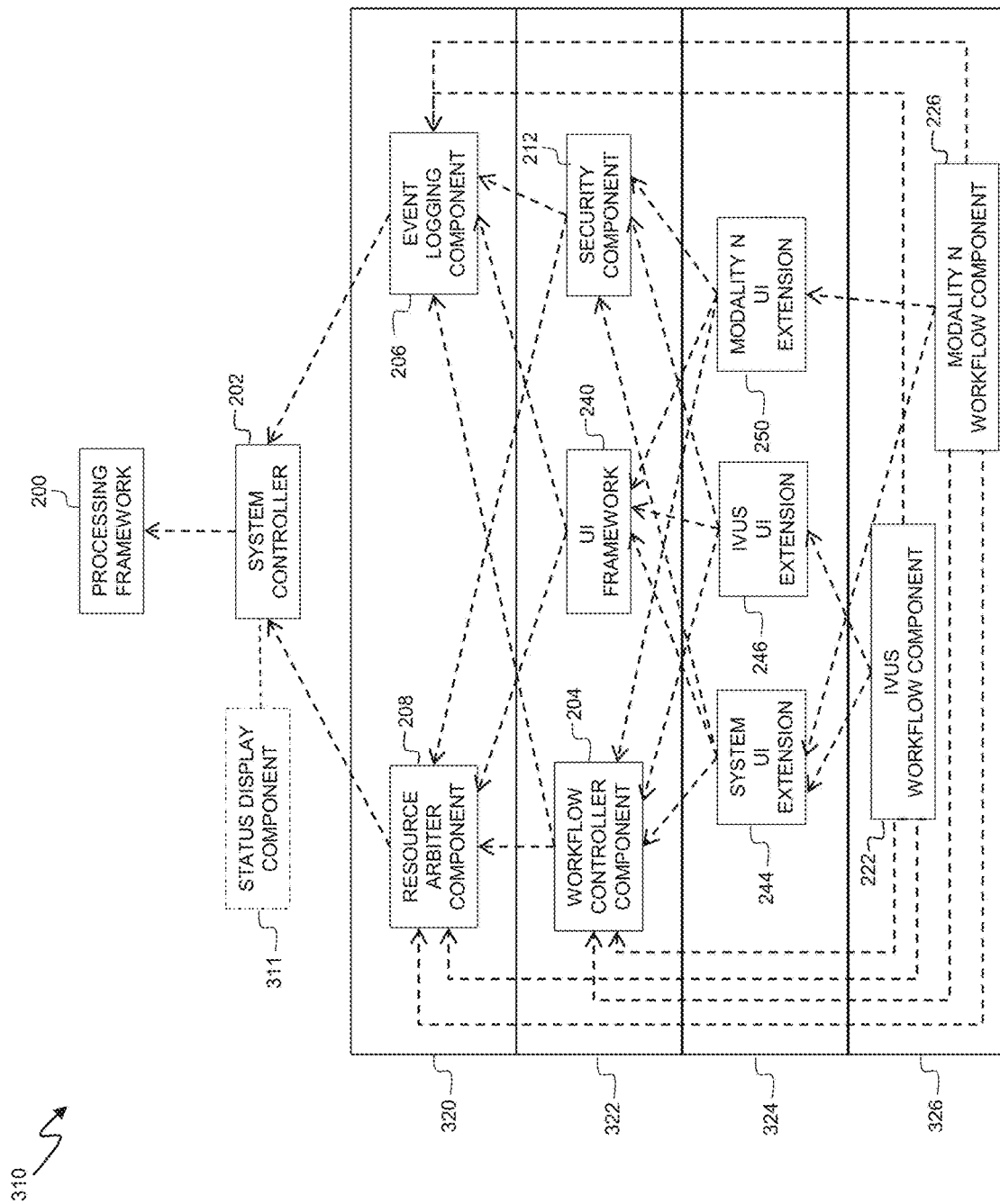
FIG. 4 illustrates an example directed graph built during the method of FIG. 3.

After the system controller 202 receives initialization and dependency information for executable components in block 304, the method 300 proceeds to block 306 where the system controller 202 transforms the initialization information and the dependency information into a dependency map. Specifically, the system controller creates a data structure that includes all of the executable components to be started and represents all of the dependencies between the executable components. In various embodiments, the dependency map may be in many different forms such as a directed graph or a numerical dependency matrix. FIG. 4 illustrates an example directed graph 310 built by the system controller 202 in block 306 of method 300. The vertices of the directed graph 310 respectively represent the executable components to be started by the system controller and the edges between the vertices represent the dependencies between the components. For example, among other things, the direct graph 203 depicts the dependencies established in the example XML configuration file discussed above—i.e., the IVUS workflow component 222 depends on both the event logging component 206 and the workflow controller component 204, and the workflow controller component 204 in turn depends on the event logging component 206. The example directed graph 310 created by the system controller 202 similarly represents the interdependencies of the plurality of other components in the framework 200, such as the resource arbiter component 208, the UI framework service 240, the security component 212, the various UI extensions 244, 246, 250, and the modality workflow components 222 and 226. The directed graph 310 additionally illustrates a status display component 311 coupled to the system controller 202. The system controller 202 utilizes the status display component 311 to inform users of the processing system 101 about the startup status of the system via a display device such as the main controller 120 or bedside controller 118. In one embodiment, the status display component 311 is an executable component independent of other components in the framework such that the system controller may start and utilize its interfaces during system startup before the main UI framework services are available. Further, for the sake of clarity, not all of the executable components of the framework 200 are depicted in the directed graph 310. Additionally, as mentioned above, the interdependencies represented in the directed graph 310 may also be represented by other types of data structures such as a numerical matrix that represents interdependencies between components as, for example, 0s or 1s. Further, if an executable component is listed in the configuration file but is also listed in an exception file, the executable component will not be included in the directed graph built by the system controller 202.

After the system controller 202 has built the dependency map in block 306, the method proceeds to decision block 312 where it is determined whether the dependency map contains any cyclic dependencies. Specifically, the system controller 202 searches the dependency map for two or more executable components that depend on each other. In such a scenario, it may be impossible to determine a "correct" startup order. If cyclic dependencies exist in the dependency map, the system controller 202 logs the error in block 314 and the system is powered-off. If no cyclic dependencies exist in the dependency map, the method 300 continues to block 316 where the system controller 202 derives the start order of the executable components indicated by the initialization information. In one embodiment, the system controller 202 may perform a depth-first, topological sort on the dependency map to derive a start order in which no component will be started before another component upon which it depends. In the illustrated example of FIG. 4, the directed graph 310 has been subject to a depth-first, topological sort. Specifically, as a result of the sort, the executable components are placed into startup levels 320, 322, 324, and 326 that group components from least dependent to most dependent. For example, the top startup level 320 includes the resource arbiter component 208 and the event logging component 206 because they depend only on the system controller 202. In contrast, the bottom startup level 326 includes the IVUS workflow component 222 and the modality "N" workflow component 226 because they depend on components in each of the other startup levels either primarily or secondarily.

Figure 5:
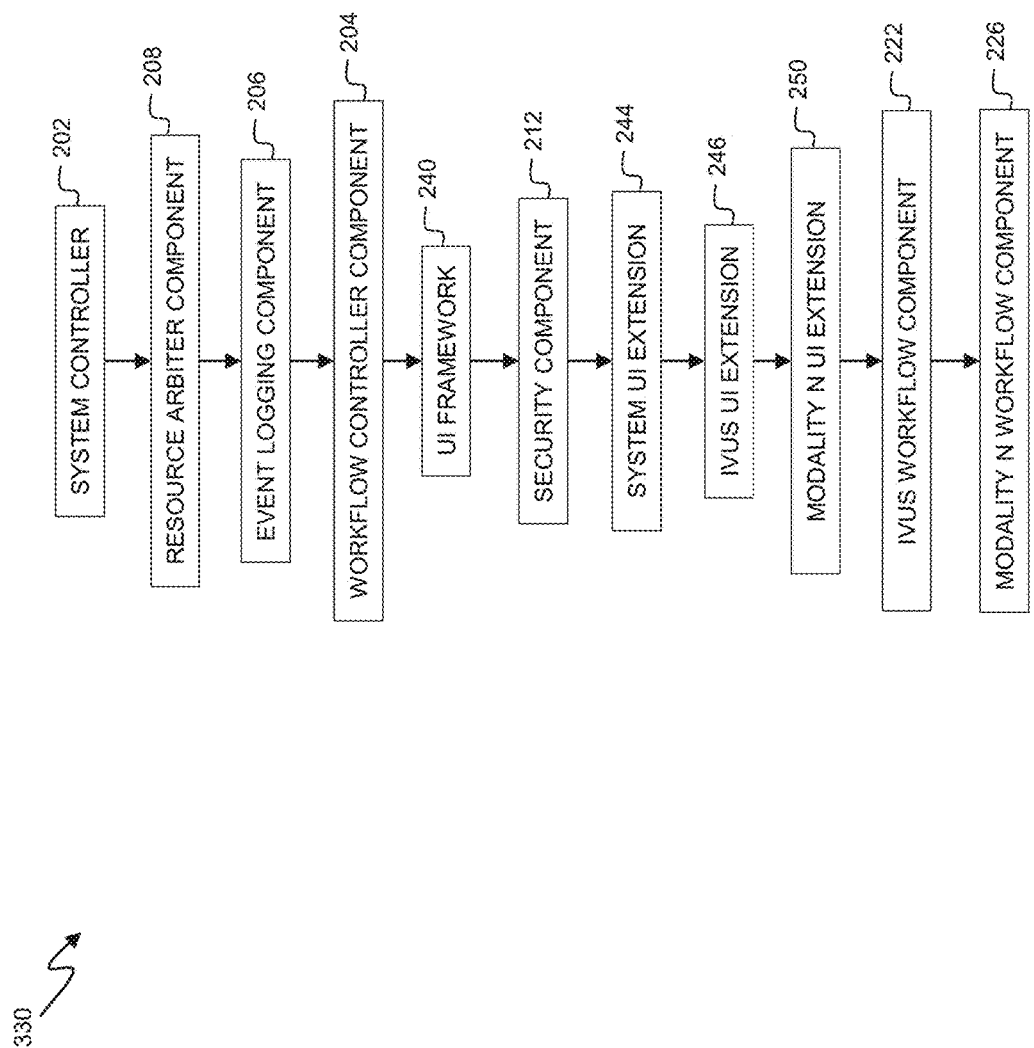
FIG. 5 illustrates an example start order vector based on the example directed graph of FIG. 4.

The system controller 202 utilizes the startup levels 320, 322, 324, and 326 to determine a startup order. Specifically, all components in the top-most startup level 320 should be started before all components in the second startup level 322, and all the components in the second startup level 322 should be started before all the components in the startup level 324 and so forth. In some embodiments, the startup order of components within each level may be arbitrary because they are not dependent upon one another. In such a scenario, the system controller 202 may randomly assign a start order for components within each level or, in alternative embodiments, the system controller may start all components within a start level concurrently. However, in other embodiments, the system controller 202 may build a start order vector that represents a strict sequential startup order for all executable components to be started. For example, FIG. 5 illustrates an example start order vector 330 that comprises an ordered list of the executable components to be started. In one embodiment, the system controller 202 builds the start order vector 330 using the topologically-sorted directed graph 310 and additional factors, such as component priority, to determine a start order of executable components within the same startup level. One of ordinary skill in the art would recognize that the start order vector 330 is simply an example and it may be ordered in a variety of different manners depending on many factors, and further, that the system controller 202 may utilize other data structures to hold a start order derived from the dependency map built in block 306 of method 300.

Once a start order is determined in block 316, the system controller 202 starts the executable components in the processing framework 200 according to the start order in block 332. Each executable component is started according to its initialization information, such as command line parameters, received by the system controller 202 in block 304. As an aspect of this, once an executable component is started, the system controller 202 waits for all interfaces of the component to become available before starting the next component in the start order. In one embodiment, each executable component is required to broadcast a "Process Ready" message (or data transfer object) to the system controller 202 to indicate that it has published all of its interfaces.

Further, the system controller 202 is configured to log the progress of the startup sequence including the success or failure of each executable component started. In certain embodiments, during the initial phases of the startup sequence, before the event logging component 206 has been started, the system controller 202 may log messages using a limited internal logging library. Then, after the event logging component 206 has been started, the system controller 202 may send status messages via the message delivery component 210 to the event logging component to be logged. Such status messages may include the "Process Ready" messages (or data transfer objects) issued by the executable components.

In one embodiment, as the system controller 202 is initializing the executable components during system startup in block 332, it may display the status of the startup sequence to users on a display device coupled to the processing system 101 via the status display component 311. Specifically, in some instances, the system controller 202 may call the status display component 311 to display a splash screen on the main controller 120 and/or bedside controller 118 while the system controller is starting the executable components. In some embodiments, the splash screen may be static, but in other embodiments, the splash screen may display the startup status of each executable component as it is being initialized by the system controller 202 including any errors encountered. For instance, the status display component 311 may display on a display device a first information screen related to the startup status of a first executable component and then update the display device such that it displays a second information screen related to the startup status of a second executable component.

In decision block 334, it is determined whether all interfaces of all the executable components are available, for instance by inspecting Process Ready messages. If all components in the start order vector have not successfully been started, the method 300 returns to block 332 to wait for all interfaces to become available or, if core system components such as the workflow controller component 204 could not be started, the system controller 202 may initiate a shutdown sequence for the processing system 101. If, instead, all components in the start order vector have successfully been started, the method 300 continues to block 336 where the system controller 202 monitors the status of the components as they execute during operation of the processing system 101. As one aspect of this, the system controller 202 may listen for errors and exceptions thrown by the executable components and if, such errors or exceptions are critical, initiate a shutdown (and optional restart) of the executable component.

The system controller 202 will continue to monitor the executable components in the processing framework 202 until it receives a system shutdown signal, as shown in block 338. At that point, the method 300 moves to block 340 where the system controller 202 stops the executable components it started in block 332. In one embodiment, the system controller 202 stops the components in the reverse order in which it started them, however, in alternative embodiments, it may stop the components in an order based on additional and/or different factors such as each component's current processing state. Further, in certain embodiments, the system controller may utilize the status display component 311 to display information about the status of the shutdown sequence on a display device coupled to the processing system 101. Additionally, during shutdown, the system controller may be configured to log the shutdown status of each executable component via the event logging component 206 or an internal logging library if the event logging component has already been shut down.

After the system controller 202 has shut down all of the executable components for which it is responsible, the method 300 moves to decision block 342 where it is determined whether a system restart has been requested. If so, the method returns to block 304 where the system controller 202 receives component initialization and dependency information, which may or may not be different than the information received during the initial startup sequence. If a restart is not requested, the method terminates at block 344, where the processing system 101 is powered-off.

It is understood that the method 300 for a dependency-based startup sequence of a multi-modality processing system is simply an example embodiment, and in alternative embodiments, additional and/or different steps may be included in the method. For example, in one embodiment, after receiving component and initialization and dependency information in block 304, the system controller 202 may determine whether medical sensing devices associated with executable components are communicatively coupled to the processing system and whether such devices are in working order. If medical sensing devices associated with executable components are not available to acquire medical sensing data, the system controller 202 may exclude the associated components from the dependency map created in block 306 and skip initialization of such components. Further, in certain embodiments, monitoring components in block 336 may include detecting whether executable components associated with medical sensing devices communicatively coupled to the processing system 101 are responsive to medical sensing data received from the devices. If such components are found to be non-responsive, the system controller 202 may stop or restart the components. Additionally, the method 300 may be applied to different types of processing systems such as diagnostic systems associated with collecting and processing MRI data or systems utilized in computer assisted surgery (CAS) applications. Further, the method 300 may be applied to perform a dependency-based startup of a network-based processing framework in which executable components are distributed across multiple, remotely located computer systems. Still further, as discussed above in association with FIG. 2, an extension, such as for a specific modality, may include an extension controller that controls the executable components associated with the extension. Such an extension controller may implement portions of method 300 to startup the executable components in an appropriate order based upon their interdependencies. Though, unlike the system controller 202, an extension controller would not be operable to startup or shutdown the entire multi-modality processing system.

Although illustrative embodiments have been shown and described, a wide range of modification, change, and substitution is contemplated in the foregoing disclosure and in some instances, some features of the present disclosure may be employed without a corresponding use of the other features. Further, as described above, the components and extensions described above in association with the multi-modality processing system may be implemented in hardware, software, or a combination of both. And the processing systems may be designed to work on any specific architecture. For example, the systems may be executed on a single computer, local area networks, client-server networks, wide area networks, internets, hand-held and other portable and wireless devices and networks. It is understood that such variations may be made in the foregoing without departing from the scope of the present disclosure. Accordingly, it is appropriate that the appended claims be construed broadly and in a manner consistent with the scope of the present disclosure.

What is claimed is:

1. A dependency-based startup method in a multi-modality medical processing unit, the method comprising:

receiving, by a system controller of the multi-modality medical processing unit, initialization information about:
a resource arbiter component configured to manage sharing of system resources,
a workflow controller component configured to govern a multi-modality medical sensing workflow,
a first medical sensing modality component configured to communicate with a first medical sensing device configured to be coupled to the multi-modality medical processing unit, and
a second medical sensing modality component configured to communicate with a second medical sensing device configured to be coupled to the multi-modality medical processing unit;

receiving, by the system controller, dependency information about the resource arbiter component, the workflow controller component, and the first and second medical sensing modality components, wherein the dependency information indicates that both the first medical sensing modality component and the second medical sensing modality component depend on the resource arbiter component and the workflow controller component;

deriving, by the system controller, a start order based on the dependency information;

determining, by the system controller, whether the first medical sensing device is coupled to the multi-modality medical processing unit;

determining, by the system controller, whether the second medical sensing device is coupled to the multi-modality medical processing unit; and starting the resource arbiter component, the workflow controller component, and the first and second medical sensing modality components in the multi-modality medical processing unit according to the start order, wherein the first medical sensing modality component is only started when the first medical sensing device is coupled to the multi-modality medical processing unit, and wherein the second medical sensing modality component is only started when the second medical sensing device is coupled to the multi-modality medical processing unit.

2. The method of claim 1, wherein the first medical sensing modality component is associated with one of intravascular ultrasound (IVUS) imaging, intravascular photoacoustic (IVPA) imaging, optical coherence tomography (OCT), forward looking IVUS (FL-IVUS), fractional flow reserve (FFR), coronary flow reserve (CFR), or angiography.

3. The method of claim 1, wherein the start order comprises a plurality of startup levels organized such that the first and second medical sensing modality components occupy the same startup level and such that the first and second medical sensing modality components come later in the start order than the resource arbiter component and the workflow controller component.

4. The method of claim 1, wherein the resource arbiter component and the workflow controller component are started during every startup sequence.

5. The method of claim 1, wherein starting the resource arbiter component, the workflow controller component, and the first and second medical sensing modality components includes displaying startup status information on a display device communicatively coupled to the multi-modality medical processing unit.

6. The method of claim 1, wherein receiving initialization information and receiving dependency information includes reading a configuration file having initialization information and dependency information stored therein.

7. The method of claim 6, wherein the configuration file is an XML document encoded according to a defined schema.

8. The method of claim 1, further comprising detecting whether at least one of the first medical sensing modality component or the second medical sensing modality component is responsive to medical sensing data.

9. The method of claim 8, further comprising stopping or restarting any medical sensing modality component found to be unresponsive.

10. A multi-modality medical system, comprising:
a multi-modality medical processing unit, including:
  a resource arbiter component configured to manage sharing of system resources,
  a workflow controller component configured to govern a multi-modality medical sensing workflow,
  a first medical sensing modality component configured to communicate with a first medical sensing device configured to be coupled to the multi-modality medical processing unit,
  a second medical sensing modality component configured to communicate with a second medical sensing device configured to be coupled to the multi-modality medical processing unit; and
a system controller configured to:
  receive initialization information about the resource arbiter component, the workflow controller component, and the first and second medical sensing modality components,
  receive dependency information about the resource arbiter component, the workflow controller component, and the first and second medical sensing modality components, wherein the dependency information indicates that both the first medical sensing modality component and the second medical sensing modality component depend on the resource arbiter component and the workflow controller component,
  derive a start order based on the dependency information,
  determine whether the first medical sensing device is coupled to the multi-modality medical processing unit,
  determine whether the second medical sensing device is coupled to the multi-modality medical processing unit, and
  start the resource arbiter component, the workflow controller component, and the first and second medical sensing modality components in the multi-modality medical processing unit according to the start order, wherein the first medical sensing modality component is only started when the first medical sensing device is coupled to the multi-modality medical processing unit, and wherein the second medical sensing modality component is only started when the second medical sensing device is coupled to the multi-modality medical processing unit.

11. The system of claim 10, wherein the first medical sensing modality component is associated with one of intravascular ultrasound (IVUS) imaging, intravascular photoacoustic (IVPA) imaging, optical coherence tomography (OCT), forward looking IVUS (FL-IVUS), fractional flow reserve (FFR), coronary flow reserve (CFR), or angiography.

12. The system of claim 10, wherein the start order comprises a plurality of startup levels organized such that the first and second medical sensing modality components occupy the same startup level and such that the first and second medical sensing modality components come later in the start order than the resource arbiter component and the workflow controller component.

13. The system of claim 10, wherein the resource arbiter component and the workflow controller component are started during every startup sequence.

14. The system of claim 10, wherein starting the resource arbiter component, the workflow controller component, and the first and second medical sensing modality components includes displaying startup status information on a display device communicatively coupled to the multi-modality medical processing unit.

15. The system of claim 10, wherein receiving initialization information and receiving dependency information includes reading a configuration file having initialization information and dependency information stored therein.

16. The system of claim 15, wherein the configuration file is an XML document encoded according to a defined schema.

17. The system of claim 16, wherein the system controller is further configured to: detect whether at least one of the first medical sensing modality component or the second medical sensing modality component is responsive to medical sensing data.

18. The system of claim 17, wherein the system controller is further configured to: stop or restart any medical sensing modality component found to be unresponsive.

19. The system of claim 10, further comprising:
the first medical sensing device, wherein the first medical sensing device comprises a guidewire or a catheter configured to be positioned within the body of a patient.

20. The system of claim 19, further comprising:
the second medical sensing device.

* * * * *